(12) United States Patent
Tajima et al.

(10) Patent No.: US 7,947,967 B2
(45) Date of Patent: May 24, 2011

(54) METHOD FOR EVALUATING A SEMICONDUCTOR SUBSTRATE

(75) Inventors: Michio Tajima, Kanagawa (JP); Hiroki Sugimoto, Kanagawa (JP)

(73) Assignee: Japan Aerospace Exploration Agency, Tokyo (JP)

( * ) Notice: Subject to any disclaimer, the term of this patent is extended or adjusted under 35 U.S.C. 154(b) by 553 days.

(21) Appl. No.: 12/037,744

(22) Filed: Feb. 26, 2008

(65) Prior Publication Data

US 2008/0213926 A1 Sep. 4, 2008

(30) Foreign Application Priority Data

Feb. 26, 2007 (JP) .................. 2007-045411

(51) Int. Cl.
*G01N 21/63* (2006.01)
*H01L 21/66* (2006.01)
(52) U.S. Cl. ...................... 250/492.2; 438/16
(58) Field of Classification Search .................. 438/16; 250/492.2
See application file for complete search history.

(56) References Cited

U.S. PATENT DOCUMENTS 7,141,790 B2 * 11/2006 Koguchi et al. ............... 250/308

FOREIGN PATENT DOCUMENTS

| JP | 03 001553 | 1/1991 |
| JP | 05-129402 | 5/1993 |
| JP | 10-233384 | 9/1998 |
| WO | WO 2007/005438 A2 | 1/2007 |

OTHER PUBLICATIONS

Trupke, T., et al. "Photoluminescence imaging of silicon wafers," 2006, pp. 1-3, Applied Physics Letters 89, 044107, American Institute of Physics.

Yablonovitch, E., et al. "Unusually Low Surface-Recombination Velocity on Silicon and Germanium Surfaces," Jul. 14, 1986, pp. 249-252, vol. 57, No. 2, Physical Review Letters, The American Physical Society, Bell Communications Research, Murray Hill, New Jersey, 07974.

European Search Report, EP 08 00 3500, Reference No. J 2922EU—ro, Application No. 08003500.9-1234, mailed May 26, 2008, 7 pages.

Sugimoto H., et al., "Photoluminescence Analysis of Intra-Grain Defects in Cast-Grown Polycrystalline Silicon Wafers," Materials Science in Semiconductor Processing, Elsevier Science Publishers, B.V., Barking, UK vol. 9, No. 1-3, Feb. 1, 2006, pp. 102-106.

(Continued)

*Primary Examiner* — Evan Pert
(74) *Attorney, Agent, or Firm* — Blakely, Sokoloff, Taylor & Zafman LLP.

(57) ABSTRACT

A method for evaluating a semiconductor substrate is provided that can evaluate even a thin semiconductor substrate or a substrate with untreated surfaces, can evaluate a large quantity of semiconductor substrates for solar cells in a short time and can be used as in-line inspection in a production process of solar cells or the like. The method for evaluating a semiconductor substrate comprises a step of immersing a semiconductor substrate in an etching solution filled in a container, a step of irradiating the substrate being immersed in the etching solution with light via the etching solution to cause the substrate to emit photoluminescence, and a step of observing the emitted photoluminescence.

2 Claims, 2 Drawing Sheets

OTHER PUBLICATIONS

Sugimoto H., et al., "Analysis of Intra-Grain Defects in Multicrystalline Silicon Wafers by Photoluminescence Mapping and Spectroscopy," Japanese Journal of Applied Physics, Part 2 (Letters), Japan Society of Applied Physics, vol. 45, No. 25, Jul. 2006, XP002479524, ISSN: 0021-4922, pp. L641-L643.

Sugimoto H., et al., "Photoluminescence Imaging of Multicrystalline Si Wafers during HF Etching," Japanese Journal of Applied Physics, Part 2 (Letters), Japan Society of Applied Physics Through the Institute of Pure and Applied Physics Japan, vol. 46, No. 12-16, Apr. 2007, XP002479525, ISSN: 0021-4922, pp. L339-L341.

European Examination Report for EP Counterpart Patent Application No. 08 003 500.9-1234, 4 pgs., (Aug. 26, 2009).

* cited by examiner (a)     (b)    5 mm (a)     (b)    5 mm

METHOD FOR EVALUATING A SEMICONDUCTOR SUBSTRATE

CROSS-REFERENCE TO RELATED APPLICATIONS

The present patent application claims priority from Japanese Patent Application No. 2007-045411, filed on Feb. 26, 2007.

BACKGROUND OF THE INVENTION (i). Field of the Invention

The present invention relates to a method for evaluating a semiconductor substrate. In particular, it relates to a method for evaluating a semiconductor substrate that makes it possible to measure the photoluminescence (PL) distribution of a semiconductor substrate used in a solar cell or the like at high speed and high resolution.

(ii) Description of the Related Art

Production of silicon solar cells has been increasing rapidly. To improve the photoelectric conversion efficiency of the silicon solar cell, it is urgently needed to improve the crystallinity of a silicon substrate used in the solar cell.

To attain high photoelectric conversion efficiency in solar cells, it is essential that carriers (electrons and holes) generated by light irradiation reach electrodes without recombining on the way to the electrodes. That is, it can be said that the conversion efficiency of the solar cell is determined directly by such parameters as the lifetime and diffusion length of the carriers, and a method for evaluating these parameters is needed.

Meanwhile, as causes for recombination of the carriers, crystalline structural defects such as grain boundaries and dislocations and impurity-contaminated parts that exist in a silicon substrate are conceivable. In other words, when crystalline structural defects and/or impurities exist in the silicon substrate, it is expected that the lifetime and/or diffusion length of the carriers are/is shortened, resulting in a decrease in the photoelectric conversion efficiency of the solar cell.

Accordingly, to obtain a solar cell having high photoelectric conversion efficiency, a method for evaluating distributions of crystalline structural defects like dislocations that exist in a silicon substrate and the extent of contamination by impurities as well as the method for evaluating the lifetime and diffusion length of the carriers is important.

As a method for evaluating the diffusion length of carriers (minority carriers in particular), a surface photovoltage method (SPV method) is available. This method is a method which measures the diffusion length of the carriers of a semiconductor sample such as a wafer by irradiating the sample with light of multiple wavelengths and detecting a surface potential change at that time by means of a noncontact probe placed near the sample.

However, this method is inconvenient in that it requires preparation of a relatively thick sample (generally 1 mm or thicker) for making an accurate measurement.

Meanwhile, as a method for evaluating the lifetime of minority carriers, a microwave photoconductivity decay method (μ-PCD method) is available. This method is a method which measures the lifetime of the carriers of a semiconductor sample by irradiating the sample with light and detecting a conductivity change at that time by means of a microwave. In particular, this method is often used for evaluation of contamination of silicon wafer.

However, this method is inconvenient in that it requires subjecting the surfaces of the sample to a special treatment such as an iodine ethanol treatment prior to the measurement. Consequently, a method of inhibiting surface recombination by hydrogen fluoride gas etching may be used in measuring the lifetime of the carriers of a semiconductor substrate by the μ-PCD method. However, this method requires a large-scale system for the gas etching.

Both of the above SPV method and μ-PCD method have a problem that measurement of two-dimensional carrier lifetime distribution within a sample wafer surface not only requires a stage for scanning the sample in the XY direction but also takes time because the measurement must be made while scanning the sample. The measurement time is as long as several tens of minutes per sample. Further, a low spatial resolution of several millimeters at most is also a problem.

Further, when a silicon substrate used in a solar cell or the like is to be evaluated by the above μ-PCD method or SPV method, the silicon substrate must be withdrawn from a production process of the solar cell or the like once, placed on the XY stage, placed in gas etching equipment if necessary, and evaluated over a long time. Therefore, this method cannot be used as in-line inspection of silicon substrates in a production process of solar cells or the like.

With a measurement method with spatial resolution of millimeter order such as the above μ-PCD method or SPV method, distribution of defects whose size is in micron order such as crystalline structural defects cannot be evaluated. That is, although low crystallinity of a silicon substrate can be evaluated macroscopically by these conventional methods, these methods cannot be used to evaluate what causes the low crystallinity of the silicon substrate microscopically. In this regard, it can be said that the conventional methods cannot provide information about improving the crystallinity of the silicon substrate sufficiently.

A photoluminescence (PL) imaging method developed in recent years is expected as a next-generation evaluation method that evaluates the characteristics of a silicon substrate with treated surfaces for production of a solar cell or the like in a short time of about 1 second or less and with a high spatial resolution of several tens of micrometers. In particular, since the method has high spatial resolution and crystalline defect distribution clearly emerges on a PL image as dark lines, it is expected to be very helpful as a measure for improving crystallinity. Further, it is known that PL intensity distribution obtained by the PL imaging method well-matches carrier lifetime distribution and diffusion length distribution obtained by the μ-PCD method and the SPV method.

However, the conventional PL imaging method has the following problem when a substrate with untreated surfaces is an object to be measured. That is, since photoluminescence to be detected is greatly influenced by surface recombination of the carriers in the substrate, accurate measurement becomes difficult and PL intensity lowers, so that measurement time becomes at least several tens of times longer than that when a substrate with treated surfaces is measured. This problem is particularly noticeable when the thickness of a substrate is small, and measurement is extremely difficult even when considerable time is spent therefor.

Patent Literature 1
  Japanese Patent Laid-Open Publication No. 1993-129402.
Non-Patent Literature 1
  T. Trupke, R. A. Bardos, M. C. Schubert and W. Warta, "Photoluminescence imaging of silicon wafers" Applied Physics Letters 89, 044107 (2006).
Non-Patent Literature 2
  E. Yablonovitch, D. L. Allara, C. C. Chang, T. Gmitter and T. B. Bright, "Usually Low Surface-Recombination Velocity on Silicon and Germanium Surfaces" Physical Review Letter 57, p. 249 (1986).

In recent years, the thickness of a semiconductor (silicon) substrate for a solar cell has been reduced. This indicates that the influence of surface recombination of the carriers of a semiconductor substrate has become greater upon evaluation of the substrate. In this regard, the conventional PL imaging method is assumed to be unable to make accurate measurement easily because it is significantly influenced by recombination when a semiconductor substrate has small thickness or is not surface-treated. Further, since PL intensity lowers due to the influence of surface recombination, longer measurement time is required to obtain information sufficient to evaluate a semiconductor substrate by the conventional PL imaging method.

Further, along with a sharp increase in production of silicon solar cells, a technique that makes it possible to evaluate a large quantity of silicon substrates for solar cells in a short time has been demanded. Higher efficiency can be achieved if a method for evaluating a semiconductor substrate can be used as in-line inspection in a production process of solar cells or the like.

Further, a more accurate evaluation can be expected if a semiconductor substrate can be evaluated in a condition similar to a condition in which the semiconductor substrate is actually used in a solar cell or the like. For instance, in the conventional µ-PCD method in which the surfaces of a substrate are treated with hydrofluoric acid before the lifetime of the carriers of the substrate is measured, the sample substrate is subjected to an iodine ethanol treatment immediately after the substrate is taken out of hydrofluoric acid, so as to prevent degradation of the surface condition of the surface-treated substrate before the measurement. However, according to a finding by the present inventors, degradation of the surface condition of the surface-treated substrate starts rapidly from the moment the sample substrate is taken out of hydrofluoric acid for the surface treatment. This indicates that only substrates with some degree of deterioration in surface condition can be evaluated with the conventional method.

Further, when a substrate is evaluated by the PL imaging method and measurement must be made in a state of strong excitation because the measurement takes a long time, there is a possibility that characteristics in a condition different from a condition in which the substrate is actually used are seen because the substrate is evaluated in an environment different from actual light intensity at the time of operation of solar cell. In particular, when a substrate whose carrier lifetime is short is evaluated, measurement in strong excitation is unavoidable with the conventional method due to low signal strength, and this problem is noticeable.

Therefore, an object of the present invention is to provide a method for evaluating a semiconductor substrate that can evaluate even a thin semiconductor substrate or a substrate with untreated surfaces by inhibiting surface recombination of the carriers of the substrate.

Another object of the present invention is to provide a method for evaluating a semiconductor substrate that can evaluate a large quantity of semiconductor substrates for solar cells in a short time and can be used as in-line inspection in a production process of solar cells or the like.

Still another object of the present invention is to provide a method for evaluating a semiconductor substrate that makes it possible to evaluate a semiconductor substrate in a condition similar to a condition in which the semiconductor substrate is actually used in a solar cell or the like, from the viewpoints of the surface condition of the substrate to be evaluated and the intensity of light to be radiated.

SUMMARY OF THE INVENTION

The present inventors have focused attention on a fact that a semiconductor substrate is subjected to etching, in particular, acid etching using hydrofluoric acid or the like, in a production process of the semiconductor substrate used in a solar cell or the like and have achieved the present invention based on a finding that the above problems can be solved by use of an etching solution's effect of inhibiting surface recombination of the carriers of the substrate by conducting PL imaging concurrently with this etching.

That is, the present invention provides a method for evaluating a semiconductor substrate that comprises a step of immersing a semiconductor substrate in an etching solution filled in a container, a step of irradiating the substrate being immersed in the etching solution with light via the etching solution to cause the substrate to emit photoluminescence, and a step of observing the emitted photoluminescence.

In the method of the present invention, the etching solution is preferably an acidic etching solution selected from the group consisting of hydrofluoric acid, hydrochloric acid, phosphoric acid, sulfuric acid, trifluoromethanesulfonic acid, and a mixture of two or more of these acids.

Further, in the method of the present invention, the step of observing the emitted photoluminescence may include a step of observing the two-dimensional distribution of the crystalline structural defects of the semiconductor substrate.

As described above, the present invention uses an etching solution used in an etching step that is one of steps for producing a silicon substrate used for a solar cell or the like and has achieved accurate measurement of the PL distribution of a substrate by use of the etching solution's effect of inhibiting surface recombination of the carriers of the substrate by carrying out PL imaging of the silicon substrate with the substrate immersed in this etching solution.

The effects of the present invention can be summarized as follows.

(1) According to the present invention, surface recombination of the carriers of a semiconductor substrate can be inhibited by immersing the substrate in an etching solution. Consequently, a high-speed and high-resolution evaluation of PL distribution can be made even on a substrate with untreated surfaces, a thin substrate having a thickness of not larger than 200 µm, and a silicon ingot section, whose accurate measurement has been difficult with the conventional PL imaging method.

(2) Further, as a result of inhibition of the surface recombination of the carriers of the substrate and a dramatic increase in PL intensity, the measurement is hardly affected by noises, and the measurement time can also be reduced dramatically. Since a large quantity of substrates must be evaluated in the industry, it is an extremely significant advantage that a substrate can be evaluated within 1 second, for example. According to the present invention, a very-high-speed and high-resolution evaluation can be made within 1 second per substrate and with a spatial resolution of several tens of micrometers.

(3) The present invention makes it possible to evaluate a substrate with the substrate immersed in an etching solution by use of an etching step which is generally included in production steps and without preparing special equipment. That is, the method of the present invention uses one of the steps for producing a semiconductor substrate and requires no special processing and can therefore be applied to in-line inspection. Further, although PL measurement is an optical measurement method, the etching solution used in the present invention does not affect the measurement since it is transparent. In addition, the PL imaging measurement is free from dynamic elements, and a semiconductor substrate can be evaluated in a static state and non-contact manner throughout the measurement. Accordingly, no care needs to be taken for a possibility that the etching solution may be spilled by shaking.

(4) Further, in the present invention, since a substrate is evaluated with the substrate immersed in an etching solution, it is possible to carry out the measurement without deterioration in the surface condition of the substrate.

(5) Further, being able to make a measurement in a shorter time than when the conventional method is used indicates that measurement in weaker excitation is possible if the same time as that taken by the conventional method may be taken. By use of the method of the present invention, it becomes possible to evaluate a semiconductor substrate even in weak excitation, and it becomes possible to evaluate a semiconductor substrate in a condition similar to a condition in which the semiconductor substrate is actually used in a solar cell or the like or in weaker excitation than the similar condition as required.

(6) As applications of the present invention, high-speed and high-resolution evaluations of the defect distribution, minority carrier lifetime distribution and impurity concentration distribution of a semiconductor substrate are conceivable.

DETAILED DESCRIPTION OF THE PREFERRED EMBODIMENTS

Figure 1:
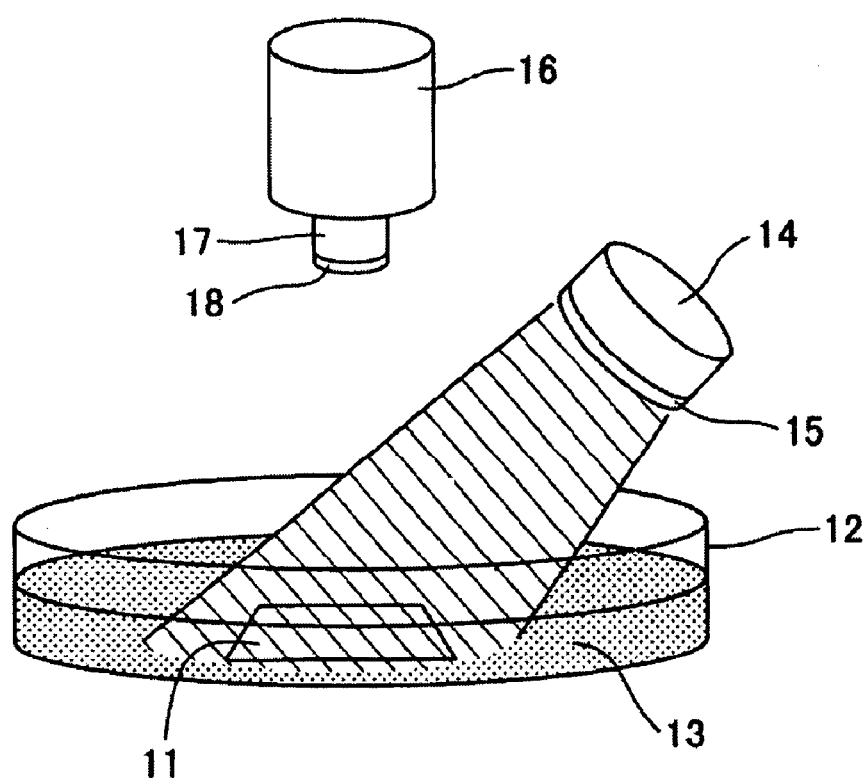
FIG. 1 is a schematic block diagram illustrating an exemplary system configuration used in an evaluation method according to the present invention.

FIG. 1 is a schematic block diagram illustrating an exemplary system configuration used in the evaluation method according to the present invention.

A sample semiconductor substrate 11 which is an object to be evaluated is immersed in an etching solution 13 that is filled in a container 12 such as a plastic petri dish.

As the etching solution 13, any etching solution which is used in an etching step that is one of steps for producing a silicon substrate used for a solar cell or the like can be used. However, to obtain a good surface recombination inhibiting effect, the etching solution is desirably an acidic etching solution selected from the group consisting of hydrofluoric acid, hydrochloric acid, phosphoric acid, sulfuric acid, trifluoromethanesulfonic acid, and a mixture of two or more of these acids. It is particularly preferable to use hydrofluoric acid as the etching solution.

Photoluminescence is observed with the sample semiconductor substrate 11 being immersed in the etching solution 13 in the container 12. The depth of the etching solution 13 in the container 12 is such that the sample semiconductor substrate 11 can be immersed therein, and it is considered that a depth of about 5 mm is generally sufficient. The shape of the sample semiconductor substrate 11 may be any shape such as a circular or rectangular shape. The surfaces of the sample semiconductor substrate 11 are desirably flat. However, pits and projections with which a camera used for observation of photoluminescence can still be focused are acceptable.

As an excitation light source 14 for irradiating the sample semiconductor substrate 11 immersed in the etching solution 13 with light via the etching solution 13, a light source having a larger energy wavelength (generally 350 to 900 nm) than the forbidden band gap of silicon, e.g. a light emitting diode array, can be used. It is also possible to use a laser or laser diode as the light source 14. It is desirable that a filter 15 such as an infrared cut filter be attached to the light source 14.

As a photoluminescence detector 16 for observing photoluminescence emitted from the sample semiconductor substrate 11, an electronically cooled CCD camera can be used, for example. Before the objective lens 17 of the detector 16 is preferably placed a band-pass filter 18 that cuts excitation light (e.g. wavelength of 900 nm and shorter) from the light source 14 but transmits photoluminescence (e.g. wavelength of 900 nm and longer) from the sample semiconductor substrate 11 therethrough.

Further, when hydrofluoric acid is used as the etching solution 13, for example, it is preferable that a cover (not shown) made of transparent plastic or the like be inserted between the detector 16 and excitation light source 14 and the container 12, because hydrofluoric acid may corrode the lens 17, filter 18 and filter 15.

When a transparent container is used as the container 12, it is possible that the sample semiconductor substrate 11 is irradiated with light from the light source 14 from beneath or the side of the container 12 and a photoluminescent image is taken by the detector 16 such as a camera from beneath or the side of the container 12. Further, photoluminescence of the sample semiconductor substrate 11 can generally pass through the sample semiconductor substrate 11 itself. Therefore, it is also possible that the sample semiconductor substrate 11 is irradiated with light from the light source 14 from the back side of the sample semiconductor substrate 11 and a photoluminescent image is taken by the detector 16 such as a camera which is disposed on the front side of the sample semiconductor substrate 11.

EXAMPLES

In the system configuration of FIG. 1, a 5% hydrofluoric acid (HF) aqueous solution was used as an etching solution 13, a light emitting diode array was used as an excitation light source 14, and an electronically cooled CCD camera was used as a detector 16, to observe photoluminescence from a sample semiconductor substrate 11.

As the sample semiconductor substrate 11, a multicrystalline silicon substrate having a resistivity of 1.1 Ωcm, a thickness of 310 μm and a size of 4 cm×4 cm was used. A circular plastic container having a diameter of 8 cm was used as the container 12, and the etching solution was filled in the container to a height of about 5 mm from the bottom of the container.

As the light emitting diode array, 28 Luxeon V Stars (wavelength: 500 nm) of Philips Lumileds Lighting Company were used. At the front of the light emitting diode array 14, an infrared cut filter 15 (which cuts a wavelength of 600 nm and longer) was placed.

As the electronically cooled CCD camera 16, an infrared sensitizing type having 1024×1024 pixels and an operation temperature of −70° C. was used. Further, as a lens for the electronically cooled CCD camera 16, an industrial lens having a focal length of 25 mm and F1.4 was used. At the front of this lens, an infrared transmission filter 18 (which transmits a wavelength of 830 nm and longer therethrough) was placed.

Reference Example

Firstly, a change in photoluminescence intensity with time was determined for a case when photoluminescence was observed with the sample semiconductor substrate immersed in the 5% HF aqueous solution, a case when photoluminescence was observed after the sample semiconductor substrate was etched with the 5% HF aqueous solution and then immersed in pure water and a case when photoluminescence was observed after the sample semiconductor substrate was etched and then exposed to air. The results are shown in FIG. 2.

Figure 2:
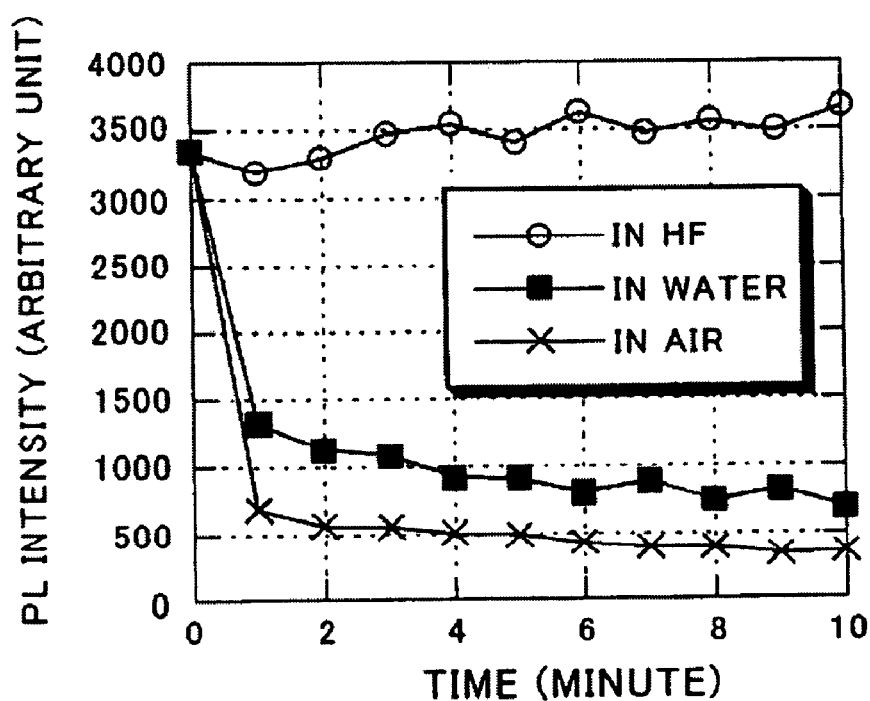
FIG. 2 is a graph illustrating changes in photoluminescence intensity with time when a sample semiconductor substrate is immersed in an HF aqueous solution, when a sample semiconductor substrate is immersed in pure water and when a sample semiconductor substrate is placed in air.

It is seen from the results of FIG. 2 that while photoluminescence of sufficient intensity was constantly observed even if time passed when photoluminescence was observed with the sample semiconductor substrate immersed in the HF aqueous solution, photoluminescence intensity sharply decreased within one minute when the sample semiconductor substrate was placed in pure water or air after etched. This decrease in photoluminescence intensity is assumed to be attributed to degradation of the surface condition of the sample semiconductor substrate. It is assumed that this supports a fact that when the lifetime of the carriers of a substrate is measured by a conventional μ-PCD method, for example, only the substrate with the surface condition degraded to a certain degree can be evaluated, even if the sample substrate is taken out of hydrofluoric acid and immediately subjected to an iodine ethanol treatment before measurement after a substrate surface treatment with hydrofluoric acid. In all cases, the sample semiconductor substrate was etched with the 5% HF aqueous solution for 10 minutes at the beginning. This etching treatment is a treatment for inhibiting surface recombination of carriers, and although a distinct effect is still attained by etching which lasts for about 1 minute, the etching was carried out for 10 minutes in the above cases so as to treat the sample semiconductor substrates sufficiently.

Further, the observations were made with the concentration of the HF aqueous solution changed to 2.5%, 5%, 10% and 20%. Although the effect was seen at all of the above concentrations, the effect was the most remarkable at 5%.

Comparative Example 1

Figure 3:
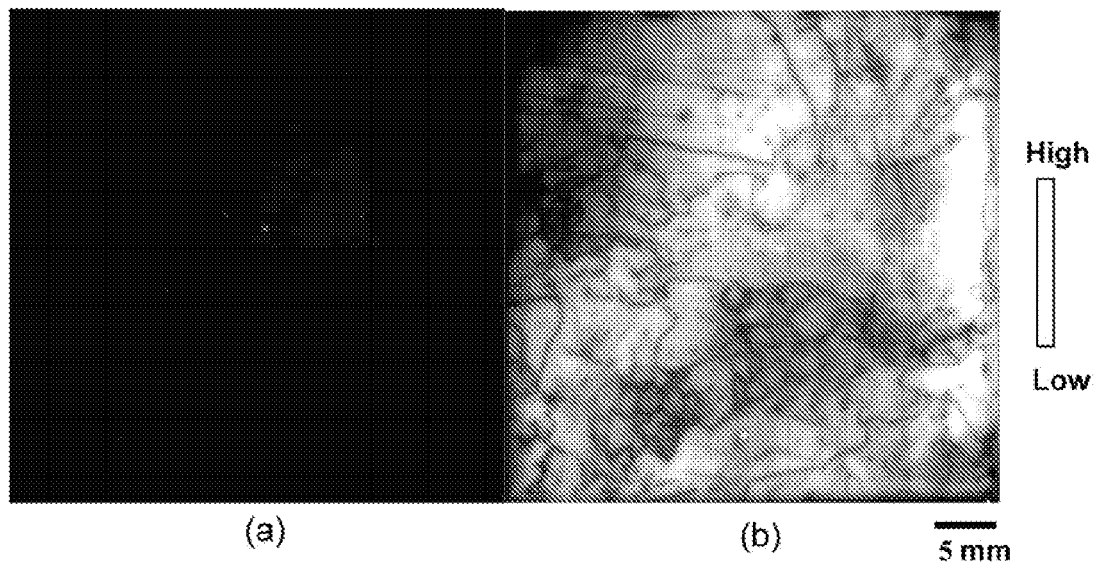
FIG. 3 illustrates PL images, wherein (a) is a PL image obtained by a method of Comparative Example and (b) is a PL image obtained by a method of the present invention.

A sample silicon semiconductor substrate having a thickness of 310 μm was prepared. Without immersing the substrate in an HF aqueous solution, a PL image obtained by excitation by light from a light emitting diode array with a measurement time of 1 second and a spatial resolution of 70 μm was taken by an electronically cooled CCD camera. The result is shown in FIG. 3(a). The two-dimensional distribution of the crystalline structural defects of the sample semiconductor substrate could not be observed.

Example 1

A PL image obtained under the same conditions as those in the above Comparative Example 1 except that photoluminescence was observed with the sample semiconductor substrate immersed in the 5% HF aqueous solution is shown in FIG. 3(b). The two-dimensional distribution of the crystalline structural defects of the sample semiconductor substrate was clearly obtained.

Comparative Example 2

Figure 4:
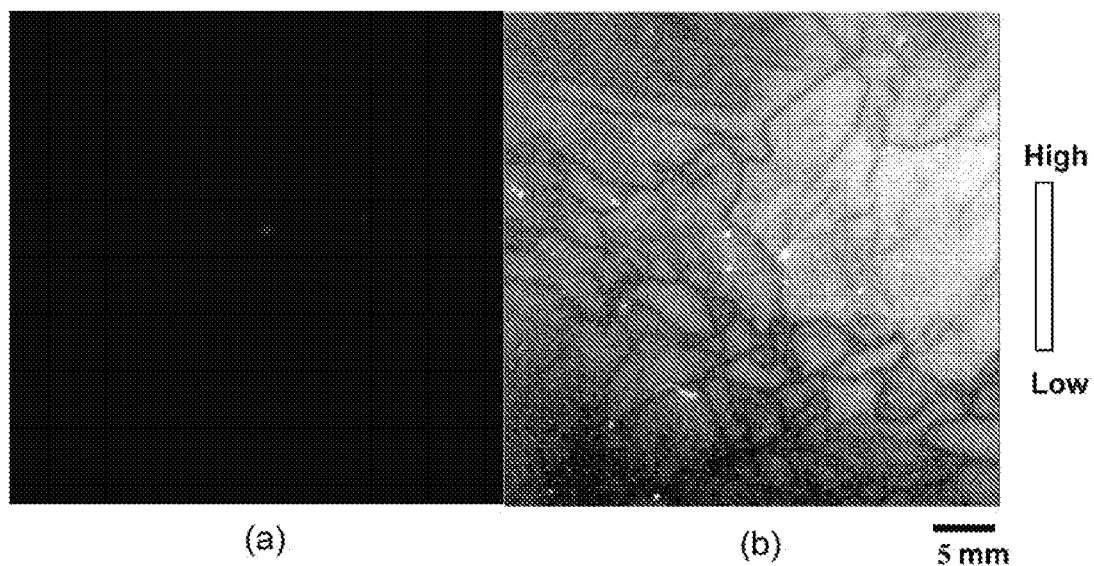
FIG. 4 illustrates PL images, wherein (a) and (b) are PL images obtained by methods of Comparative Examples.

A PL image obtained under the same conditions as those in the above Comparative Example 1 except that the measurement time was increased to 50 seconds and the spatial resolution was decreased to 140 μm is shown in FIG. 4(a). The two-dimensional distribution of the crystalline structural defects of the sample semiconductor substrate still could not be observed.

Comparative Example 3

A PL image obtained under the same conditions as those in the above Comparative Example 2 except that the thickness of the sample semiconductor substrate was increased to 1,600 μm is shown in FIG. 4(b). When the substrate was not immersed in the HF aqueous solution, the two-dimensional distribution of the crystalline structural defects of the sample semiconductor substrate was observed for the first time, when the sample had thickness which was at least 5 times larger than that of the sample of Example 1, the spatial resolution was reduced to ½, and the measurement time was increased to 50 times. However, the PL image is obscure and contains many noises as compared with Example 1.

The present invention can be applied to an in-line inspection system for a solar cell manufacturing process and a system for evaluating the characteristics of a silicon substrate. As applications of the present invention, high-speed and high-resolution evaluations of the defect distribution, minority carrier lifetime distribution and impurity concentration distribution of a semiconductor substrate are conceivable.

What is claimed:

1. A method for evaluating crystallinity of a semiconductor substrate, comprising:
   immersing a semiconductor substrate in an etching solution filled in a container;
   irradiating the substrate being immersed in the etching solution with light via the etching solution to cause the substrate to emit photoluminescence; and
   observing the emitted photoluminescence, wherein said semiconductor substrate is a silicon substrate, and said etching solution is hydrofluoric acid, and wherein said immersing the semiconductor substrate in the etching solution prevents the intensity of the emitted photoluminescence from reducing due to degradation of the surface condition of said semiconductor substrate.

2. The method of claim 1, wherein the observing the emitted photoluminescence includes observing the two-dimensional distribution of the crystalline structural defects of the semiconductor substrate.

* * * * *